(12) United States Patent
Larrabee et al.

(10) Patent No.: US 11,717,578 B2
(45) Date of Patent: Aug. 8, 2023

(54) UNDECYLENIC ACID-BASED NANOCARRIERS FOR TARGETED DRUG DELIVERY

(71) Applicant: University of Cincinnati, Cincinnati, OH (US)

(72) Inventors: Clifford E. Larrabee, Cincinnati, OH (US); Mary R. Warmin, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 145 days.

(21) Appl. No.: 16/637,082

(22) PCT Filed: Aug. 9, 2018

(86) PCT No.: PCT/US2018/045912
§ 371 (c)(1),
(2) Date: Feb. 6, 2020

(87) PCT Pub. No.: WO2019/032771
PCT Pub. Date: Feb. 14, 2019

(65) Prior Publication Data
US 2020/0246483 A1 Aug. 6, 2020

Related U.S. Application Data

(60) Provisional application No. 62/542,898, filed on Aug. 9, 2017.

(51) Int. Cl.
| | |
|---|---|
| A61K 47/69 | (2017.01) |
| A61P 35/00 | (2006.01) |
| A61K 9/00 | (2006.01) |
| A61K 31/133 | (2006.01) |
| A61K 31/195 | (2006.01) |
| A61K 31/4453 | (2006.01) |
| A61K 31/4965 | (2006.01) |
| A61K 31/704 | (2006.01) |
| A61K 31/7068 | (2006.01) |
| B82Y 5/00 | (2011.01) |

(52) U.S. Cl.
CPC ........ *A61K 47/6907* (2017.08); *A61K 9/0019* (2013.01); *A61K 31/133* (2013.01); *A61K 31/195* (2013.01); *A61K 31/4453* (2013.01); *A61K 31/4965* (2013.01); *A61K 31/704* (2013.01); *A61K 31/7068* (2013.01); *A61P 35/00* (2018.01); *B82Y 5/00* (2013.01)

(58) Field of Classification Search
None
See application file for complete search history.

(56) References Cited

U.S. PATENT DOCUMENTS

| | | |
|---|---|---|
| 2009/0098172 A1 | 4/2009 | Ikemoto et al. |
| 2013/0230542 A1 | 9/2013 | Merino et al. |

FOREIGN PATENT DOCUMENTS

WO 2008065652 A2 6/2008

OTHER PUBLICATIONS

D.T. Nguyen et al, Olfactory Exploration: State of the Art; European Annals of Otorhinolaryngology, Head and Neck Diseases, vol. 133, 2016, pp. 113-118.
H. Sayre et al, Mixed-Donor, alpha-Hydroxy Acid-Containing Chelates for Binding and Light-Triggered Release of Iron; Inorganic Chemistry, vol. 49, 2010, pp. 4433-4439.
J.V. Jokerst et al, Nanoparticle PEGylation for Imaging and Therapy; Nanomedicine (London, Jun. 2011), vol. 6. No. 4, pp. 715-728.
S. Siksna et al, Coniferous greenery-valuable natural raw material of biologically active substances; Medicinos Teorija ir Praktika, vol. 18, No. 2, 2012, pp. 146-148.
E. Koren et al, Multifunctional PEylated 2C5-lmmunoliposomes Containing pH-sensitive Bonds and TAT Peptide for Enhanced Tumor Cell Internalization and Cytotoxicity; Journal of Control Release, vol. 160, No. 2, Jun. 10, 2012, pp. 264-273.
Lee Jae-Ho et al "Polymerizable Vesicles 1-11 Based on a Single-Tailed Fatty Acid Surfactant: A Simple Route to Robust Nanocontainers", LANGMUIR, (Online) vol. 25, No. 3, Feb. 3, 2009, pp. 1566-1571.
Amato Alyssa et al "Comparison of Micellar and Vesicle-Based Drug Delivery Systems", Proceedings of the 2nd World Congress on New Technologies, (Online) Jun. 1, 2017, http://avestia.com/NewTech2017_Proceedings/files/paper/ICNFA/ICNFA_127.
Partial Supplementary European Search Report dated Apr. 8, 2021 in related European Patent Application No. 18844751.0.

*Primary Examiner* — Nannette Holloman
(74) *Attorney, Agent, or Firm* — Dinsmore and Shohl, LLP

(57) ABSTRACT

Targeted drug delivery systems comprising a therapeutic agent solubilized with undecylenic acid (UA)-based nanocarrier vesicles that may be polymerized or provided as an mPEG ester are provided to achieve targeted delivery of, for example, ROS-activated cytotoxic agents to cancer cells exhibiting high levels of ROS. Methods utilizing photodynamic and sonodynamic generation of ROS to enhance targeted delivery are also provided.

18 Claims, 16 Drawing Sheets

Fig. 14
Table 5

| Structure | Name | IC50 MA9 | Structure | Name | IC50 MA9 | Structure | Name | IC50 MA9 |
|---|---|---|---|---|---|---|---|---|
| (HN-phenyl, O-phenyl-OH) | 1 | 30±6 µM | (S-benzyl, O-phenyl-OH) | 7 | 12±1 µM | (N-methyl-benzyl, O-phenyl-H) | 13 | >125 µM |
| (N-methyl-benzyl, O-phenyl-OH) | 2 | 18±3 µM | (N-methyl-phenyl, O-phenyl-OH) | 8 | 0.75 µM | (N-methyl-benzyl, O-phenyl-OMe) | 14 | >125 µM |
| (N-ethyl-benzyl, O-phenyl-OH) | 3 | 23±5 µM | (N-methyl-benzyl propyl, O-phenyl-OH) | 9 | 4±3 µM | (N-methyl-benzyl, O-phenyl-OAc) | 15 | 0.8 µM |
| (N-isopropyl-benzyl, O-phenyl-OH) | 4 | 53±7 µM | (N-methyl-benzyl butyl, O-phenyl-OH) | 10 | 2±1 µM | (N-methyl-benzyl, O-phenyl-O-succinate) | 16 | 1 µM |
| (N-acyl-benzyl, O-phenyl-OH) | 5 | 88±6 µM | (N-ethyl-benzyl, O-phenyl-OH) | 11 | 11±1 µM | (N-methyl-benzyl, O-phenyl-OP(O)(ONa)₂) | 17 | 7±1 µM |
| (N-benzyl piperidine, O-phenyl-OH) | 6 | 28±3 µM | (N-piperidinyl-benzyl, O-phenyl-OH) | 12 | 0.6 µM | (EtO-phenyl-OH) | 18 | >125 µM |

Structure 8 = RAC1

Fig. 15B
Table 6
| Compound | Structure | IC$_{50}$ (μM) | Compound | Structure | IC$_{50}$ (μM) |
|---|---|---|---|---|---|
| 1 | 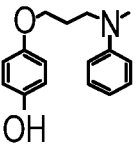 | 0.8±0.2 | 8 | 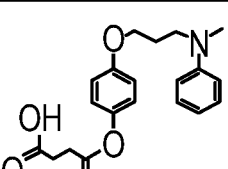 | 2.8±0.7 |
| 2 | 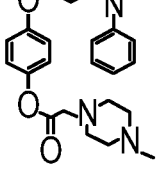 | 1±0.3 | 9 | 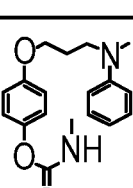 | 3.9±1 |
| 3 | 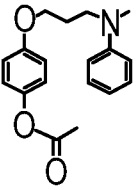 | 1±0.2 | 10 | 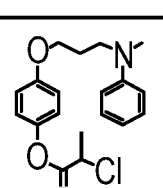 | 13±2 |
| 4 | 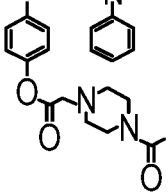 | 43±12 | 11 | 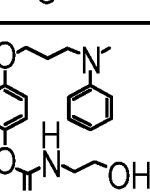 | Unstable |
| 5 | 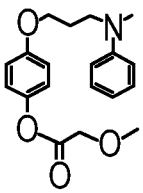 | >75 | 12 | 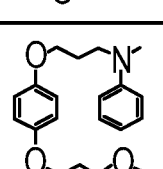 | 12±4 |
| 6 | 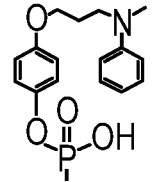 | 5±1 | 13 | 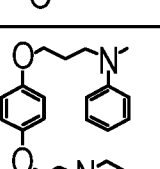 | 3.9±0.5 |
| 7 | 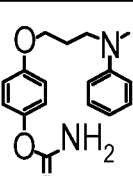 | 3±1 | 14 | 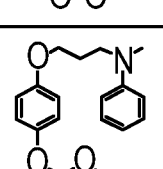 | 4±0.4 |

UNDECYLENIC ACID-BASED NANOCARRIERS FOR TARGETED DRUG DELIVERY

CROSS-REFERENCE TO RELATED APPLICATIONS

This application is a § 371 U.S. National Stage Application claiming priority to International Application No. PCT/US2018/045912 filed Aug. 9, 2018, which claims priority to U.S. Provisional Application No. 62/542,898, filed Aug. 9, 2017, each of which is incorporated herein by reference in its entirety.

BACKGROUND

Specific targeting of tumor cells has become an important strategy in the development of selective and personalized cancer therapies. Cancer cells are known to be under increased oxidative stress. The resultant relatively high level of reactive oxygen species (ROS) in cancer cells has become an intense area of focus in the design of novel therapeutic strategies to preferentially kill cancer cells over healthy cells, and in particular, in the design of ROS-activated anticancer prodrugs that selectively target cancer cells.

The high levels of ROS in cancer cells is known to be associated with cancer-cell proliferation, presence of DNA alterations, apoptosis, metastasis, angiogenesis and alteration in cellular sensitivity to anticancer agents. ROS can be found in the environment, but in cells the major source is through the mitochondrial respiratory chain. Cells with increased ROS levels are prone to exhibiting resistance to endogenous and radiation- or drug-induced cell death. Such physiological survival phenomena lead to accumulation of cancer cells with higher ROS levels. Cancer therapies, however, can be as toxic to healthy cells as to cancer cells, and a major focus in the development of new therapeutics is to exploit differences between healthy and cancer cells so that therapies can be highly targeted. One strategy has been to create small-molecule chemotherapeutics that are activated only in a low-oxygen condition and which are cytotoxic upon activation. This approach involves creating prodrugs that are activated by metabolic reduction in hypoxic conditions inducing a change to cytotoxic agents specifically in tumor environments.

ROS-associated agents have been used for many years in cancer treatment regimens; for example, both arsenic trioxide and doxorubicin generate ROS as part of their mechanism of action. Initial strategies for exploiting the elevated ROS status of cancer cells focused on the inhibition of antioxidants via potent electrophiles that inactivate glutathione (an innate antioxidant). Newer ROS associated approaches employ pro-drugs that possess, for example, a hydrogen peroxide sensitive boronic ester, which is activated upon uptake into cancer cells possessing high ROS. Another tactic that has been recently proposed involves agents that release toxic metabolites, such as iron, upon oxidation in the ROS environment. Recently, ROS-activated cytotoxic agents (RACs) were designed by some of the present inventors and found to be active against AML cancer cells. Exemplary agents are set forth in Table 5. These agents were designed to have a unique activation mechanism, which requires ROS and induce a large and bulky phenol lesion which requires DNA repair for cellular survival as part of their mechanism of action.

Recent literature has shown that AML cells are highly addicted to ROS. Excessive ROS leads to oxidative stress and may act as an important factor in AML progression. For example, an increased level of the superoxide anion radical has been observed in AML patient samples. This correlates with lower levels of antioxidants, suggesting ROS imbalance and cancer cell progression. Several genetic factors that confer ROS imbalance are also known to be associated with AML. Activating mutations or the internal tandem duplication of the FLT3 gene, a common AML genotype, leads to increased ROS. In experiments on AML lesions, RAC1 from Table 5 and FIG. 13 was found to exhibit an IC50 value of 1.8±0.3 µm, with a nine-fold greater selectivity for transformed cells compared to untransformed cells, suggesting considerable promise as a therapeutic agent.

With respect to RAC1, oxidation leads to a potent electrophile that a DNA arylamine (guanine, cytosine, adenine) can attack by 1,2-addition, followed by Michael addition and elimination to yield an unusual hydroxy-benzethenoguanine adduct. Based on this chemical mechanism, it is unlikely to be a DNA cross-linker, but nevertheless elicited a 50% loss in cell viability at 700 nM in AML cells. DNA repair is a complex process mediated by multiple different mechanisms. For DNA modifying agents, induction of double-strand breaks is a sought-after mechanism, as formation of such lesions are highly cytotoxic. RAC1 treatment was found to induce DNA strand breaks, apoptosis, and cell cycle arrest. Further, proteomic and transcriptomic studies revealed subsequent enhanced expression of the pentose phosphate pathway, DNA repair, and pathways common to cell stress. RAC1 treatment was also shown to be synergistic in combination with multiple pathway-targeting therapies in AML cells but less so in untransformed cells. These results suggest that RAC, as exemplified by RAC1, represent a promising class of therapeutic agents for selectively targeting poor prognosis AML by creating DNA double-strand breaks that require homologous recombination (see, e.g., Thowfeik, F. S., et al. A ROS-Activatable Agent Elicits Homologous Recombination DNA Repair and Synergizes with Pathway Compounds. *ChemBioChem*, 16(17), 2513-2521, 2015, the entire disclosure of which is incorporated herein).

Unfortunately, the results of in vivo studies have been less encouraging. It was found that RAC1 is degraded by oxidizing enzymes in the bloodstream prior to reaching the target cancer cells, and consequently is clinically ineffective. The use of carrier technology that shields vulnerable molecules until targeted delivery is a potential solution, but providing carriers that ensure targeted delivery of ROS-activated cytotoxic agents that are not themselves subject to premature clearance or degradation is a challenge. Further, developing a carrier technology suitable for encapsulating and effectively delivering any particular agent involves multiple unpredictable variable considerations.

It remains a compelling need in the art to develop carrier technology effective to protect ROS-activated cytotoxic agents from degradative enzymes to ensure therapeutically effective delivery and release specifically to target cancer cells.

SUMMARY

Accordingly, the present disclosure provides novel targeted drug delivery systems utilizing undecylenic acid-based nanocarrier vesicles effective for reducing the enzymatic degradation of RACs and thereby providing targeted delivery or RACs to cancer cells/tumors.

One embodiment is directed to a targeted drug delivery system comprising a chemotherapeutic agent solubilized with undecylenic acid (UA)-based nanocarrier vesicles selected from monomeric UA-based nanocarrier vesicles, polymeric UA-based nanocarrier vesicles, monomeric UA-based nanocarrier vesicles bonded to methoxy polyethylene glycol (mPEG), and polymeric UA-based nanocarrier vesicles bonded to mPEG. Pharmaceutical compositions comprising an embodiment of the drug delivery system are also provided.

Another embodiment is directed to methods of treating subjects suffering from a proliferative disorder associated with an increased presence of ROS, the method comprising administering a pharmaceutical composition comprising a targeted drug delivery system comprising a chemotherapeutic agent solubilized with undecylenic acid (UA)-based nanocarrier vesicles selected from monomeric UA-based nanocarrier vesicles, polymeric UA-based nanocarrier vesicles, monomeric UA-based nanocarrier vesicles bonded to methoxy polyethylene glycol (mPEG), and polymeric UA-based nanocarrier vesicles bonded to mPEG, said vesicles having an average hydrodynamic diameter of between about 5 and 200 nm. Chemotherapeutic agents may comprise ROS-activated agents such as ROS-activated cytotoxic agents that may be toxic to healthy cells; however administering utilizing a targeted drug delivery system ensures minimum contact with healthy cells.

Another embodiment provides pharmaceutical compositions comprising one or more of PEGylated monomeric, PEGylated polymeric UA-based nanocarrier vesicles, non-PEGylated monomeric and non-PEGylated polymeric UA-based nanocarrier vesicles complexed with at least one photoreactive ROS-generating agent or sonoreactive ROS-generating agent. Other embodiments provide method for treating cancer/tumors by administering the UA-based nanocarrier vesicles to cancer cells, for example to a tumor, and exposing the cells/tumor to photonic or acoustic energy.

These and other embodiments and aspects will be further detailed and clarified by reference to the Drawings and Detailed Description, below.

Figures are provided to illustrate particular aspects and specific embodiments and should not be construed as limiting the full scope of the invention as defined by the appended claims.

BRIEF DESCRIPTION OF THE FIGURES

FIG. 14 Table 5 setting forth intelligently designed ROS-activated cytotoxic agents (RACs)

FIG. 15B RAC1 derivatives

DETAILED DESCRIPTION

Definitions

Figure 1:
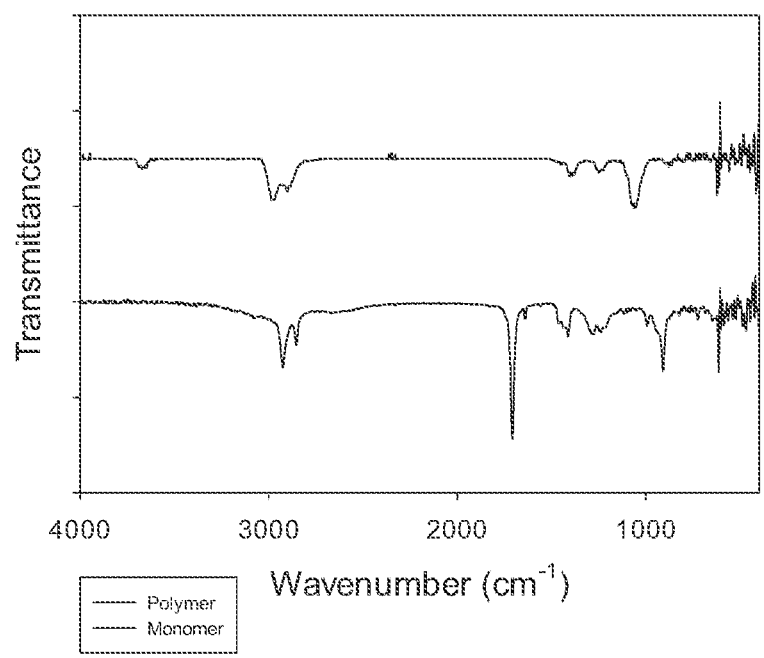
FIG. 1 IR spectra for poly(NaU) and undecylenic acid.

Oxidative stress—results from an imbalance between the production and detoxification of reactive oxygen species. The persistent oxidative stress can lead to cell damage through the oxidation of DNA, proteins and lipids. On the other hand, the intrinsic oxidative stress in cancer cells can be used for developing cancer-targeted therapies.

Reactive oxygen species—include a variety of chemically reactive molecules and free radicals derived from molecular oxygen, such as $H_2O_2$, superoxide anion ($O_2^-$), hydroxyl radical (HO.), and hypochlorite ion ($OCl^-$). The increased amount of reactive oxygen species in cancer cells lead to the increased intrinsic oxidative stress.

ROS-activated anticancer prodrugs—are compounds which are inactive, but can be converted to active anticancer drugs upon activation by reactive oxygen species (e.g., $O_2^-$, $H_2O_2$). ROS-activated anticancer prodrugs can undergo tumor-specific activation, therefore, increasing the selectivity towards cancer cells. ROS-activated cytotoxic agents are a subclass whereby the agent is cytotoxic upon activation by ROS.

Tumor-specific activation—when non-toxic prodrugs are only activated in the cancer cells through oxidation or reduction to release toxic species, while being kept intact in the normal cell environment.

Hydrodynamic diameter—is used consistent with its ordinary meaning in the art and is a standardizing particle measurement that indicates how the particle behaves in fluid, and specifically is measured by dynamic light scattering (DLS) of a hypothetical sphere that diffuses the same way as the particle being measured. Hydrodynamic diameter measurements provided herein were determined at 298 K by DLS with a Malvern Zetasizer Nano ZS. The reported diameter and standard deviation are the weighted averages of at least three measurements of the size distribution by number.

Undecylenic acid-based nanocarriers in micelle form are known in the art, and have been shown to:
- solubilize small, hydrophobic substrate molecules (Larrabee Jr, C. E. et al. (2014). Clathrate Hydrate Formation and Micellization of Tetrabutylammonium 10-Undecenoate. *International Journal of Theoretical and Applied Nanotechnology*, 2, 40-45);
- be stabilized by polymerization (Larrabee Jr, C. E., & Dennison, T. H. Micelle Formation Of Hexa (Sodium 10-Undecenoate) In Aqueous Solution: *Molecular Dynamics* and Larrabee Jr, C. E. et al. (2014, Aug. 11-13). *Effect of Oligomerization of Sodium 10-Undecenoate on the Solubilization of a Hydrophobic Substrate*. Paper presented at the International Conference on Nanotechnology: Fundamentals and Applications, Prague, Czech Republic);
- undergo pH-mediated release of the hydrophobic substrate Robison, M. et al. (Aug. 18-19, 2016). *pH-Mediated Release in a Model Drug Delivery System*. Paper presented at the Proceedings of the 2nd World Conference on Nanotechnologies (NewTech'16), Budapest, Hungary); and
- isolate substrate molecules from the aqueous environment (Ogle, E., et al. (2017). *Effect of a clathrate-forming counterion on micellar solubilization*. Paper presented at the 3rd World Congress on New Technologies (NewTech'17), Rome, Italy).

More recent studies have shown that undecylenic acid-based nanocarriers in vesicle form retain the attributes of the micelle nanocarriers, but in a larger, bilayer form. (See Amato, A., & Larrabee Jr, C. E. (2017) *Comparison of micellar and vesicle-based drug delivery systems*. Paper presented at the 3rd World Congress on New Technologies, Rome, Italy, incorporated fully herein). However, until the investigations undertaken by the present inventors, it was unknown and unpredictable as to whether UA-based nanocarriers could be designed to provide specific delivery of a therapeutic load to target cancer cells, and specifically to provide specific delivery of RAC to target cancer cells without impacting healthy cells. Vesicles were designed in the range of 10-65 nm hydrodynamic diameter, a range that is ideal for minimizing renal and kidney excretion.

Embodiments of the invention permit the use of promising therapeutic agents for the treatment of proliferative disorders that otherwise would have poor clinical efficacy due to degradation and/or inactivation prior to reaching target cancer cells/tumors, and further permit use of a non-specific cytotoxic agents by delivering such agents to target cancer cells without contacting or impacting healthy cells.

One embodiment provides a targeted drug delivery system comprising a chemotherapeutic agent solubilized with undecylenic acid (UA)-based nanocarrier vesicles selected from monomeric UA-based nanocarrier vesicles, polymeric UA-based nanocarrier vesicles, monomeric UA-based nanocarrier vesicles bonded to methoxy polyethylene glycol (mPEG), and polymeric UA-based nanocarrier vesicles bonded to mPEG, said vesicles having an average hydrodynamic diameter of between about 5 and 200 nm. According to specific embodiments, monomeric UA is polymerized, resulting in vesicles with an average hydrodynamic diameter of about 50 nm. In other specific embodiments an mPEG ester of either monomeric or polymeric UA may be formed resulting in vesicles with an average hydrodynamic diameter of about 150 nm. In very specific embodiments the mPEG-UA vesicles may be reduced in size by formulating with cholesterol and high pressure homogenization. According to more specific embodiments this results in vesicles having an average hydrodynamic diameter of about 65 nm.

According to some embodiments, the targeted drug delivery system is loaded with a therapeutic agent comprising at least one reactive oxygen species (ROS)-activated cytotoxic agent (RAC). "Loaded" as used herein can mean physically contained, bonded, or associated therewith sufficient to achieve targeted delivery. "Chemotherapeutic agent" as used herein can be a chemotherapeutic agent such as a drug or biologic, or may be in pro-drug form and activated upon delivery to the target cells. Non-limiting examples include activation by ROS such superoxide, peroxide, hydroxyl radical, singlet oxygen and alpha oxygen. In the case of RAC, the molecule is activated in the ROS environment to produce a cytotoxic agent.

Some of the present inventors previously developed an exemplary portfolio of novel RAC that share an activation mechanism. According to specific embodiments, the RAC comprises at least one molecule selected from Table 5. According to very specific embodiments, the RAC is set forth as compound 8 in Table 5, and referred to herein as RAC1. Based on initial in vitro results, RAC1 was selected for additional modification. According to specific embodiments, the RAC comprises RAC1 and/or a derivative of RAC1. In more specific embodiments, the RAC comprises at least one agent selected from Table 6.

Embodiments of the targeted drug delivery system may be formulated as a pharmaceutical composition for clinical administration. A pharmaceutical composition typically comprises one or more pharmaceutically acceptable excipients. Selection of suitable excipients is within the skill of the ordinary medicinal chemist and is based on factors such as intended route of administration, dose form, storage form, manufacturing process, intended shelf life, and the like.

Another embodiment is directed to methods of treating a subject suffering from a proliferative disorder associated with an increased presence of ROS. As discussed above in the Background, ROS is often increased in cancer cells and provides a mechanism for selective effect on cancer versus healthy cells. Proliferative disorders known to be associated with elevated ROS include melanoma, prostate, acute myeloid leukemia (AML), breast, colon, and ovarian cancer. According to specific embodiments the proliferative disorder comprises AML.

According to some embodiments, methods comprise administering a pharmaceutical composition comprising a targeted drug delivery system comprising a therapeutic agent solubilized with undecylenic acid (UA)-based nanocarrier vesicles selected from monomeric UA-based nanocarrier vesicles, polymeric UA-based nanocarrier vesicles, monomeric UA-based nanocarrier vesicles bonded to methoxy polyethylene glycol (mPEG), and polymeric UA-based nanocarrier vesicles bonded to mPEG. The vesicles comprise an average hydrodynamic diameter of between about 5 and 200 nm, between about 10 and 100 nm, between about 10 and 65 nm, between about 10 and 50 nm, between about 45 and 50 nm, or about 50 nm with a standard deviation of about 20 nm. According to specific embodiments, the UA-based nanocarrier vesicle comprises PEGylated monomeric or polymeric UA-based nanocarrier.

According to specific method embodiments therapeutic agent comprises at least one reactive oxygen species (ROS)-activated cytotoxic agent (RAC). In more specific embodiments, the RA comprises a molecule selected from Table 5, and in very specific embodiments the RAC comprises RAC1 and/or a derivative of RAC1. In other specific embodiments the agent is selected from a molecule set forth in Table 6.

Some embodiments contemplate administering at least one DNA-altering agent in conjunction with the pharmaceutical composition comprising an embodiment of the targeted delivery system. As used herein, "in conjunction with" means as a part of a therapeutic regimen, which generally refers to the course of treatment following a diagnosis. The DNA-altering agent may be administered prior to, coincident with, or subsequent to administration of the targeted delivery system. According to specific embodiments, the at least one other DNA-altering agent comprises a DNA intercalator, a DNA metabolism inhibitor, and combinations thereof. Generally, a DNA intercalator is a small molecule with a planar aromatic moiety that inserts itself between a pair of base pairs causing structural changes in DNA that lead to its functional arrest. Acridine and anthracycline type drugs are known DNA intercalators. According to very specific embodiments, the DNA intercalator comprises one or more of daunorubicin and doxorubicin, and the DNA metabolism inhibitor comprises cytosine arabinoside.

Routes of administration may be systemic, such as by intravenous injection, since the drug delivery system provides protection of the agent from degradation by enzymes that may be present in circulating fluids and from premature clearance. However, in some cases a clinician may select non-systemic administration such as via infusion as a preferred mode depending on the status of the patient.

According to some embodiments, a pharmaceutical composition comprises UA-based nanocarriers complexed with a photoreactive ROS-generating agent or a sonoreactive ROS-generating agent. The photoreactive or sonoreactive agent is delivered to target cells, and then activated by light or acoustic energy to generate ROS. ROS may then be effective for activating, a RAC, or may be effective in itself for its cytotoxic effects.

The UA-based nanocarriers of the invention may achieve concentrated amounts of photoreactive or sonoreactive agent in cancer cells/tumors by exploiting the enhanced permeability and retention effect (EPA), a passive mechanism based on achieving a size balance that permits permeability while avoiding renal clearance. Topical or transdermal delivery is also contemplated (see, e.g. Marchetti, et al. (2011). Nanocarriers and cancer therapy: approaches to topical and transdermal delivery. In *Nanocosmetics and Nanomedicines* (pp. 269-286): Springer).

In photodynamic therapy (PDT), light can be targeted to almost any part of the body using fiber optics systems and endoscopy. (See, e.g. Brown, et al. (2004). The present and future role of photodynamic therapy in cancer treatment. *The lancet oncology*, 5(8), 497-508, incorporated herein by reference.) In sonodynamic therapy, ultrasound, for example, may be applied by a probe placed on or near the skin. Sound waves are capable of deep penetration into tumor tissue and can be focused in three dimensions. (See, e.g. Canavese, G. et al. (2018). Nanoparticle-assisted ultrasound: A special focus on sonodynamic therapy against cancer. *Chemical Engineering Journal*, 340, 155-172, incorporated herein by reference.) According to specific embodiments, the photoreactive agent comprises a photosensitive iron agent. More specifically, the photoreactive agent comprises a metal chlorin species. In very specific embodiments the photoreactive agent comprises $Fe_3[diCl-Sal-AHA]_3OCH_3$ Na.

According to other specific embodiments, the sonoreactive/sonosensitive agent comprises a sonoreactive copper species. More specifically, the sonoreactive copper species comprises sodium copper chlorophyllin. In other specific embodiments, the sonosensitive species comprises copper-cysteamine (Cu—Cy) (see, e.g. Wang et al. (2018) Nanosonosensitization by using Copper-Cysteimine nanoparticles augmented sonodynamic cancer treatment, *Particle and Particle Systems Characterization*, Wiley, Vol 35, Issue 4, incorporated herein by reference).

Embodiments provide methods for selectively increasing ROS in a tumor comprising administering a pharmaceutical composition comprising UA-based nanocarriers comprising a photoreactive agent and exposing the tumor cells to light radiation/photonic energy. Exposing, for example, may be effectuated via fiber optic endoscopy. According to some embodiments, a method comprises selectively increasing ROS in a tumor, the method comprising administering a pharmaceutical composition of UA-based nanocarriers comprising a sonoreactive agent to cancer cells/a tumor and exposing the cancer cells/tumor to acoustic energy. According to very specific embodiments, the acoustic energy comprises ultrasound energy.

EXAMPLES

Example 1

The following example demonstrates that undecylenic acid-based nanocarriers (UA-based nanocarriers) have the basic physical characteristics necessary for an effective drug delivery system. Specifically, UA-based nanocarriers may be produced in a size range appropriate for exploiting the enhanced permeability and retention (EPR) effect, may encapsulate an exemplary RAC and protect the RAC from enzymatic degradation.

Materials and Methods
Polymerization of Undecylenic Acid.

Sodium 10-undecenoate was polymerized by free-radical initiation of the sodium salt of undecylenic acid (NaU) in aqueous solution above the critical micelle concentration. The product was separated by ethanol precipitation and purity was confirmed by infrared (IR) spectroscopy.

Preparation of Solutions.

Phosphate-buffered saline (PBS) was made up following the Cold Springs Harbor protocol. ("Phosphate-buffered saline (PBS)," 1970) The nanocarrier solutions were prepared by weighing poly(sodium 10-undecenoate), poly (NaU), and to the final concentration.

Hydrodynamic Diameters.

All measurements were determined at 298 K by dynamic light scattering (DLS) with a Malvern Zetasizer Nano ZS. The reported diameter and standard deviation are the weighted averages of at least three measurements of the size distribution by number.

Enzyme Kinetics.

All reactions were carried out with saturated drug in 2.06 wt %, nanocarrier solutions. RAC1 (Merino lab at University of Cincinnati) was used as received. The enzyme solution was prepared by dissolving 0.050 g of polyphenol oxidase (Worthington, 1800 u/mg) in 100 mL of PBS.

For the reactions in PBS and the poly(NaU) solutions, the enzyme-catalyzed oxidation reactions were carried out in quartz cuvettes, with 2.8 mL of the drug solution and 200 μL of the enzyme solution. Absorbance at 280 nm was automatically recorded every 0.5 minutes on a Thermo Scientific Biomate™ 3S UV-Vis spectrophotometer.

All kinetics runs showed two distinct zones, an incubation zone with a positive curvature during the first 20 minutes, followed by a consistent reaction zone with negative curvature The reactions all appeared to follow $1^{st}$-order kinetics and were analyzed by nonlinear regression data from the reaction fit to the function, $$A_t = A_0 e^{-kt} + b \tag{1}$$

where $A_t$ is the time dependent absorbance at 280 nm, $A_0$ is the initial absorbance, k is the rate constant for the reaction, t is the time in minutes and b is the extrapolated absorbance at infinite time. For a $1^{st}$-order rate law, the half-life is $$t_{1/2} = \frac{\ln(2)}{k} \tag{2}$$

Solubilization.

Beer's law calibration of RAC1 was determined in ethanol at 280 nm. Saturated solutions of the drugs were made by stirring excess amounts with the appropriate solution at least overnight and filtering.

Total exposure of drug over time. Assuming $1^{st}$-order kinetics, the area under the curve (AUC) is given by, $$AUC = \int_0^\infty A_0 e^{-kt} dt = \frac{A_0}{k} \tag{3}$$

where the concentration at time zero, $A_0$, is taken as the maximum solubility of the drug in the nanocarrier solution and the rate constant, k, is taken from the nonlinear regression results.

Polymerization

The C=C deformation absorption at 910 nm in undecylenic acid is absent (FIG. 1) in poly(NaU), indicating essentially complete polymerization.

Hydrodynamic Diameters

Figure 2:
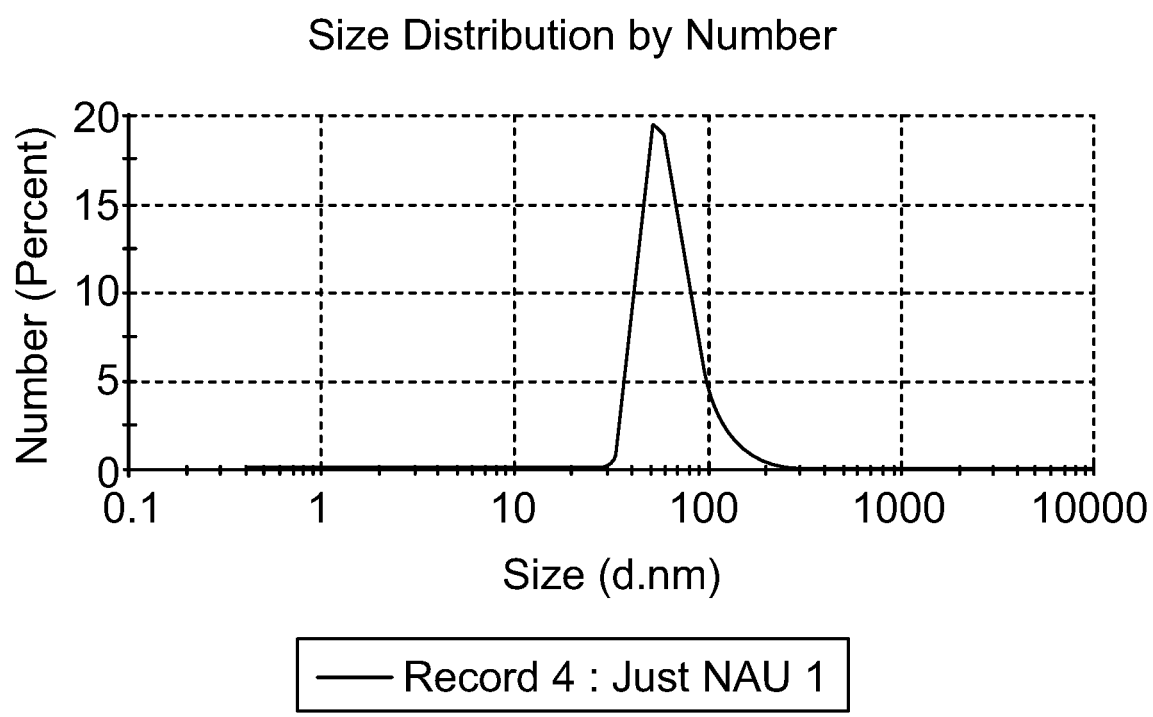
FIG. 2 Size distribution graph showing that hydrodynamic diameter of poly(NaU) has a number-average diameter of 48 nm with a standard deviation of 18 nm.

For poly(NaU) the average diameter was 48 nm with a standard deviation of 18 nm. (FIG. 2) The results are consistent with vesicle formation for the poly(NaU).

Enzyme Kinetics

Figure 3A:
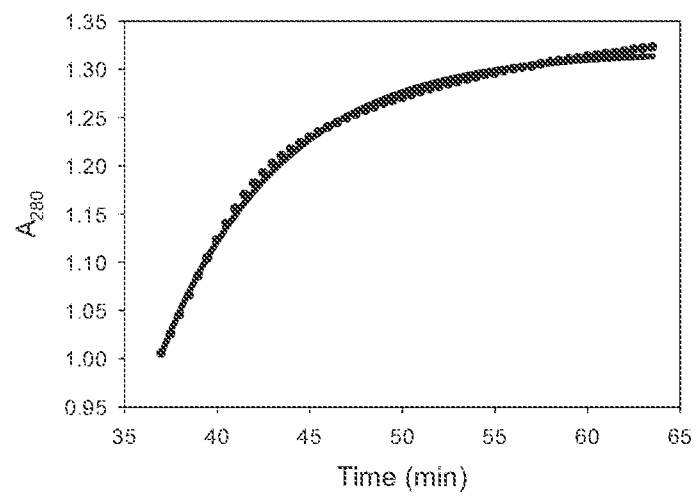
FIG. 3A and FIG. 3B Show that polyphenol oxidase catalyzed oxidation reactions of RAC1 in (left to right) PBS, poly(TBAU), and poly(NaU) solutions.
Figure 3B:
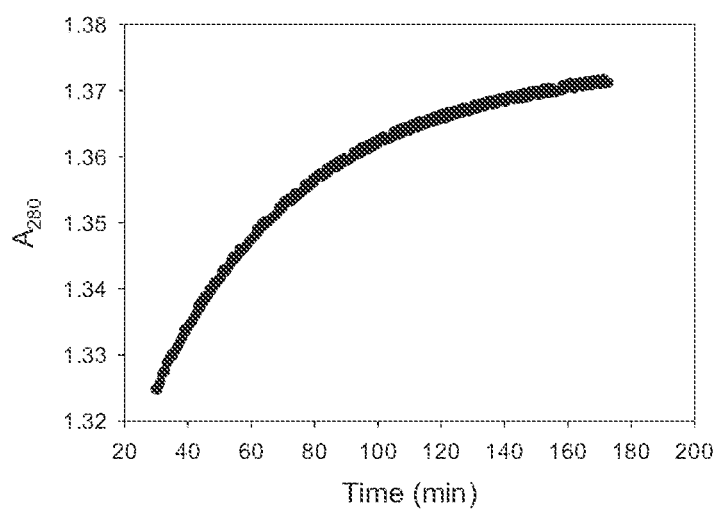

The polyphenol oxidase catalyzed reaction of RAC1 in PBS, micelle solution, and vesicle solution all follow a $1^{st}$-order rate law. (Regression of the experimental data to equation gave correlation coefficients>0.95.) The vesicle solution reduced the rate of reaction. FIGS. 3A and 3B show that polyphenol oxidase catalyzed oxidation reactions of RAC1 in (left to right) PBS, poly(TBAU), and poly(NaU) solutions.

TABLE 1

Rate constants and half-lives of enzyme catalyzed oxidation of RAC1.

| | PBS | poly(NaU) |
|---|---|---|
| k (min$^{-1}$) | 0.069 ± 0.003 | 0.0206 ± 0.0001 |
| t$_{1/2}$ (min) | 10.0 ± 0.4 | 33.6 |

Solubilization

Figure 4:
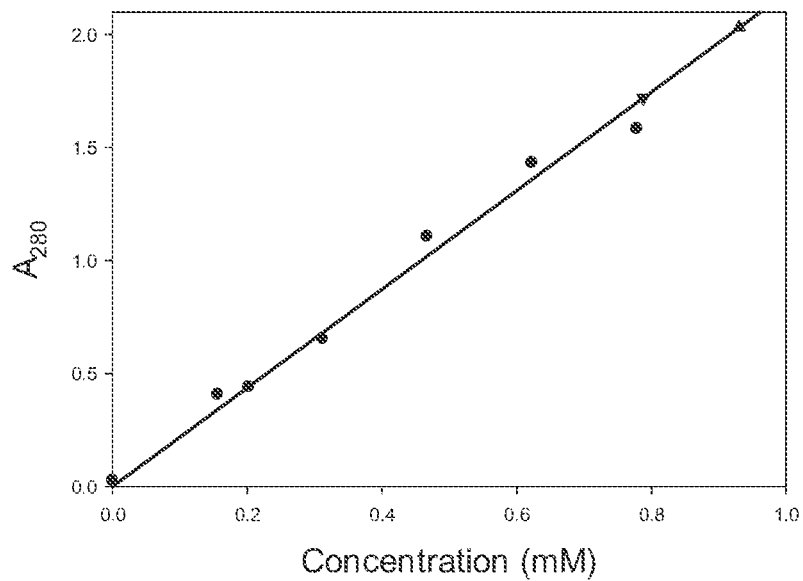
FIG. 4 Beer's Law graph for RAC1 in ethanol.
Figure 5A:
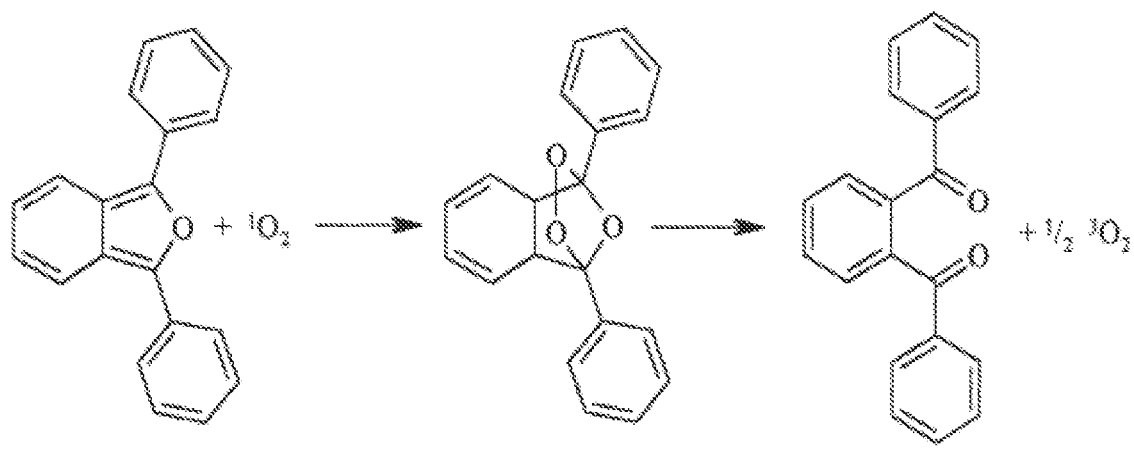
FIG. 5A Sets forth a schematic of the DPBF reaction with ROS.
Figure 5B:
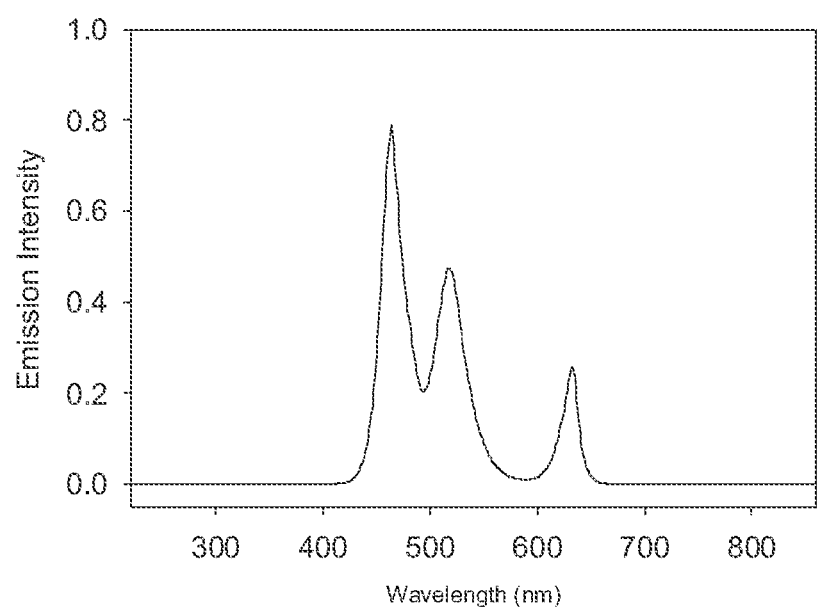
FIG. 5B shows the presence of three species in a chromatographic analysis of the DPBF analysis.

In FIG. 4, the red line is the linear regression fit to the function, A=εlc, where A is the absorbance, l is the path length (1 cm), and c in the concentration of the RAC1 (mM). The correlation coefficient is 0.99. The value of the extinction coefficient, ε, is 2.18±0.07 mM$^{-1}$.

TABLE 2

Solubility limits of RAC1.

| | PBS | poly(NaU) |
|---|---|---|
| Solubility (mM) | 0.202 ± 0.006 | 0.930 ± 0.028 |

Total Exposure of Drug Over Time.

The area under the curve for total drug exposure over time is calculated from equation 2, with the results in Table 4.

TABLE 4

Area Under the Curve.

| | PBS | poly(NaU) |
|---|---|---|
| AUC (mM · min) | 2.9 ± 0.1 | 45 ± 1 |

Sodium 10-undecenoate forms vesicles in aqueous solution in a pH range from 6.5 to 8.0. Previously it has been shown that at a concentration of 2 wt %, Transmission Electron Microscope (TEM) images show an average vesicle diameter of 26 nm. This value is about half of the hydrodynamic diameter of poly(NaU) observed here (48 nm), which is consistent with the ratio of TEM to DLS values reported for polymeric micelles of poly(styrene-alt-maleic anhydride)-b-polystyrene) of 20 nm (TEM) to 40 nm (DLS) by Baranello et al. 2015. Poly(NaU) is forming vesicles at 2.06 wt % with an average hydrodynamic diameter just under 50 nm. These vesicles are within the optimum size range for minimizing renal and kidney excretion.

Poly(NaU) vesicles significantly improve the resistance of RAC1 to polyphenol oxidase catalyzed oxidation in PBS. The half-life of the reaction is increased by a factor of two and a half and the solubility limit is increased by a factor of five. Together, increase in total exposure of the drug over time is 50-fold.

Example 2

The following Example demonstrates chemotherapeutic efficacy of RAC-loaded UA-nanocarriers, adaptability to chemical modification, and application to photodynamic and sonodynamic therapy.

(a) In Vitro Efficacy of Nanocarrier/RAC1 Chemotherapeutic Agent System

Figure 6:
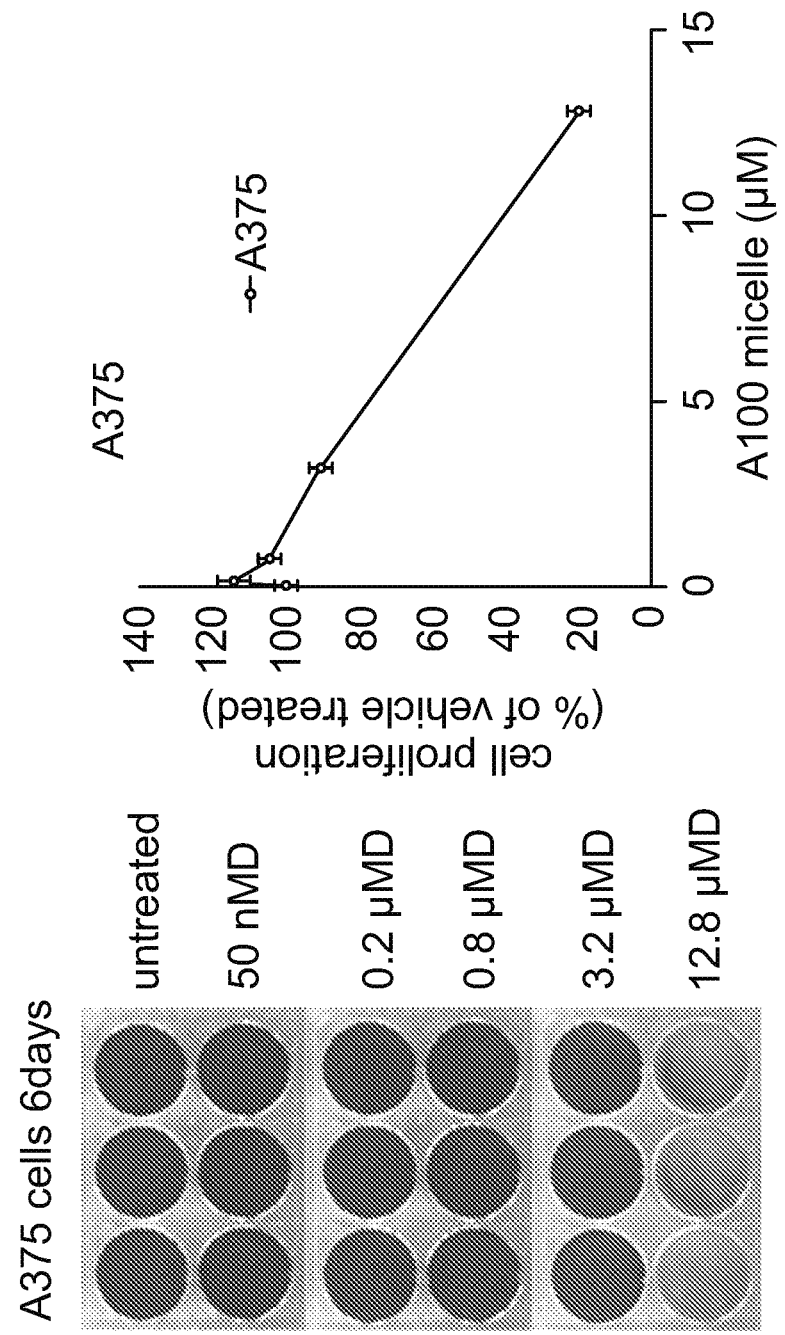
FIG. 6 Sets forth a graph of in vitro results showing cell proliferation as a function of concentration indicating that RAC-1-loaded poly(undecylenic acid) nanocarriers are effective against human malignant melanoma cells (A375) in a dose-dependent way.

Human malignant melanoma cell line MTT/A375 cell line was used to test efficacy of an RAC1-loaded UA-based nanocarrier. As shown in FIG. 6, which sets forth a graph of in vitro results showing cell proliferation as a function of concentration, RAC1-loaded poly(undecylenic acid) nanocarriers are effective against human malignant melanoma cells (A375) in a dose-dependent manner.

Figure 7:
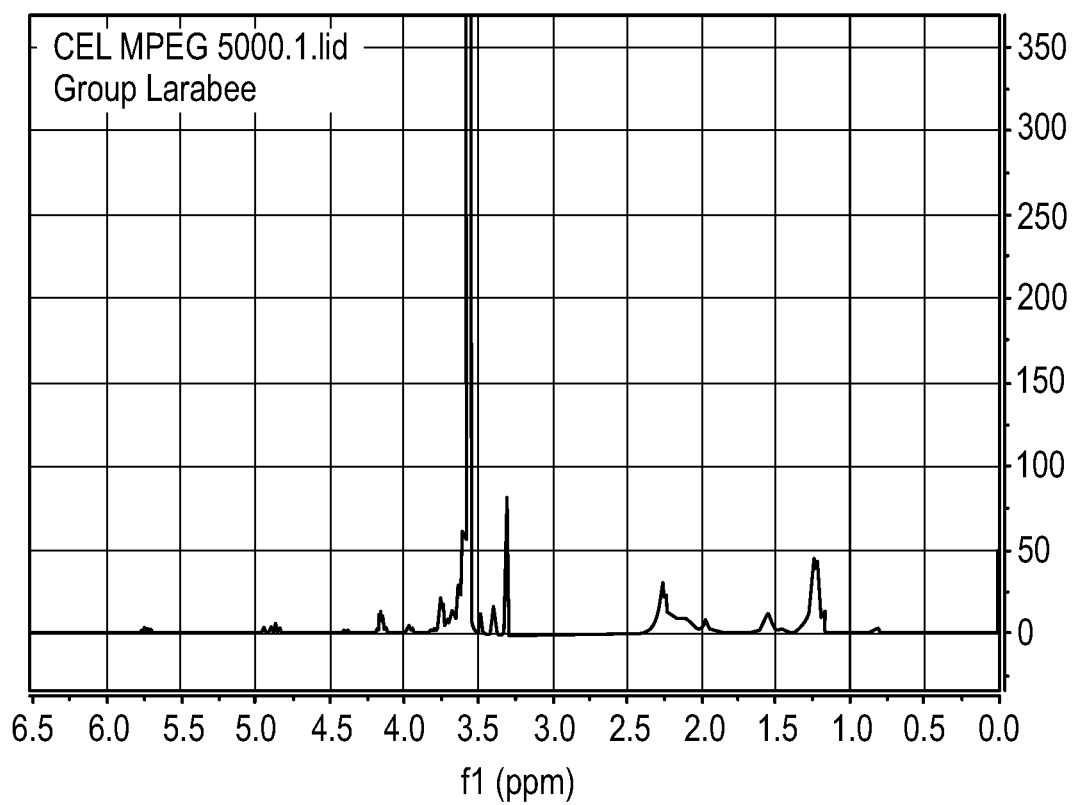
FIG. 7 A $^1$H nmr showing a peak at 4.07 ppm indicating successful esterification of the undecylenic acid; the end group analysis indicates greater than 99% purity for the mPEG-UA product.

(b) Synthesis of an mPEG Ester of Undecylenic Acid mPEG (10 g, 2.0 mmoL) was reacted with UA (10 g, 54 mmoL) at 170° C. for five hours in a melted state, following the general procedure described by Omolo. The reaction was performed under an inert nitrogen atmosphere to prevent oxidation of UA during the esterification process. Excess UA was used to ensure complete esterification of free OH in mPEG. On completion of the reaction, the reaction mixture was washed with diethyl ether (3×100 mL) to remove excess UA. The isolated solid was dried in a vacuum desiccator for 72 h to obtain mPEG-OA conjugate white dry powder (6.2 g, 60%). The product was characterized by $^1$H NMR (Bruker AV 400). As shown in FIG. 7, an $^1$H nmr shows a peak at 4.07 ppm indicating successful esterification of the undecylenic acid; the end group analysis indicates greater than 99% purity for the mPEG-UA product.

Figure 8:
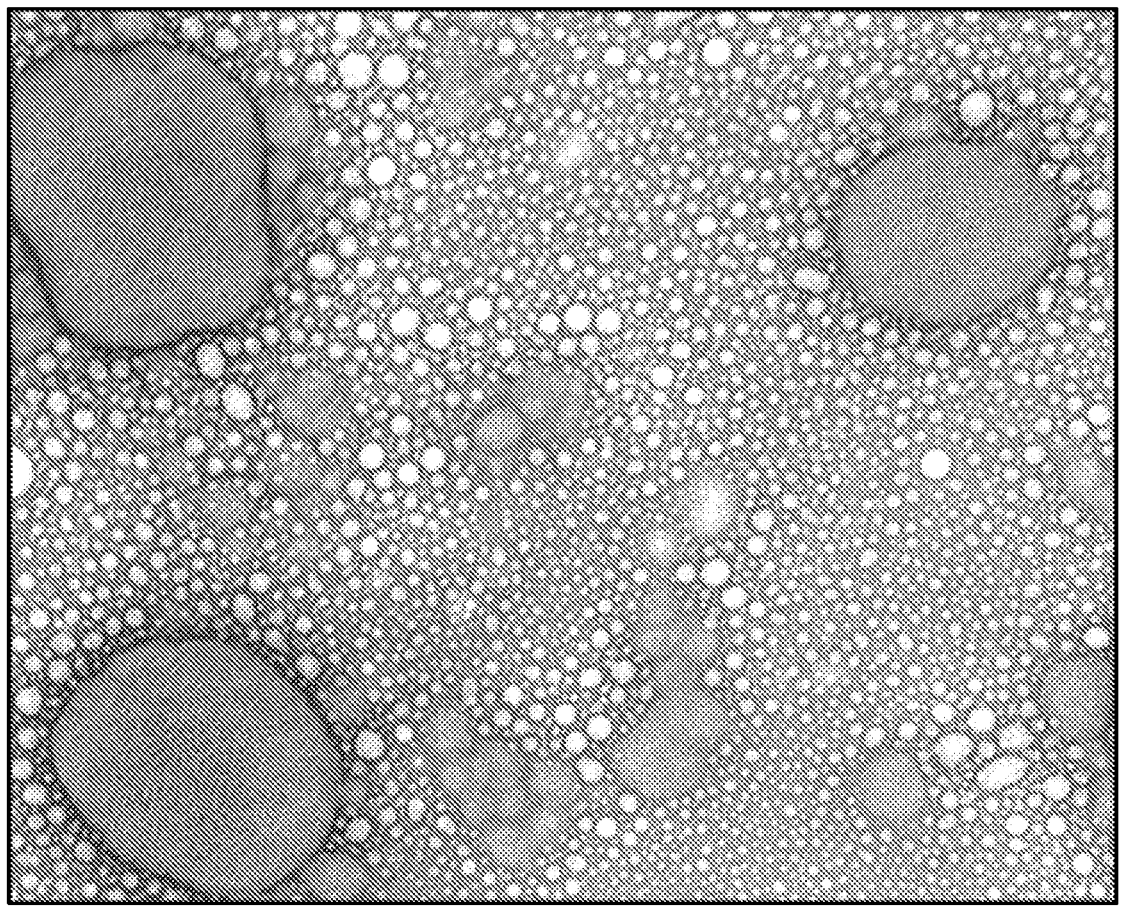
FIG. 8 Transmission electron microscope image indicating vessel formation with an average diameter of about 150 nm.

(c) The mPEG-UA Ester Forms Nanocarriers mPEG-UA nanocarriers were prepared in ASTM Type II water by ultrasonic dispersion (40 kHz, 120 W, 30 minutes) and characterized by Transmission Electron Microscopy (JEOL JEM-1230. UranyLess (Electron Microscopy Services) negative stain. 0.1% dispersions). As shown in FIG. 8, vessels formed having an average diameter of about 150 nm.

(d) mPEG-UA Nanocarriers Protect Resveratrol from Enzymatic Oxidation

Figure 9:
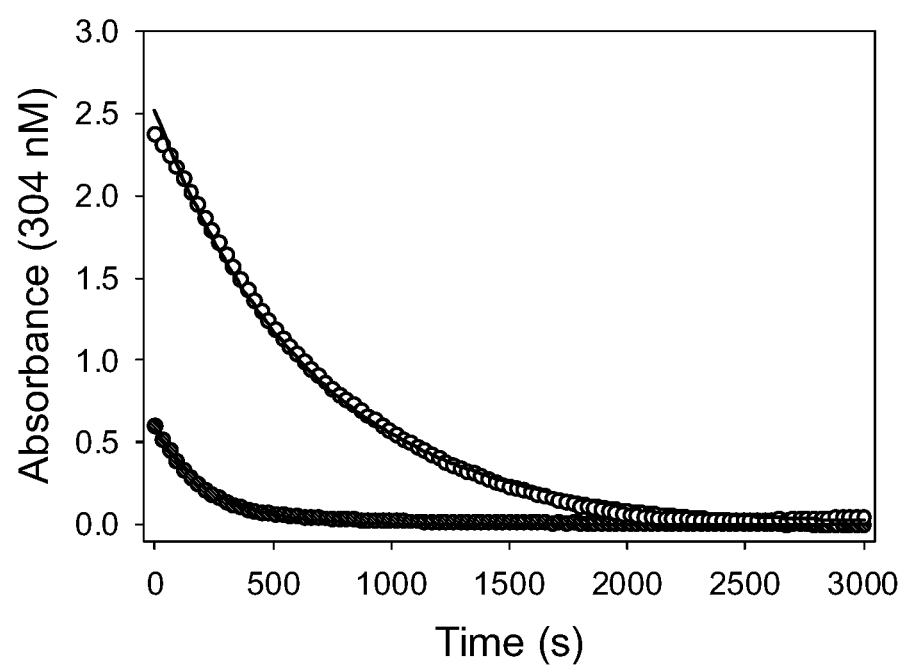
FIG. 9 Time versus absorbance graph showing that mPEG-UA encapsulated resveratrol (open circles) has a half-life 3× that of unprotected resveratrol (closed circles).

Enzyme kinetics procedures and analysis followed the protocol described in Example 1 with mPEG-UA nanocarriers and a natural product, resveratrol, as the exemplary chemotherapeutic agent. A time versus absorbance graph showing that mPEG-UA encapsulated resveratrol (open circles) has a half-life 3 times that of unprotected resveratrol (closed circles) is set forth as FIG. 9.

Figure 10:
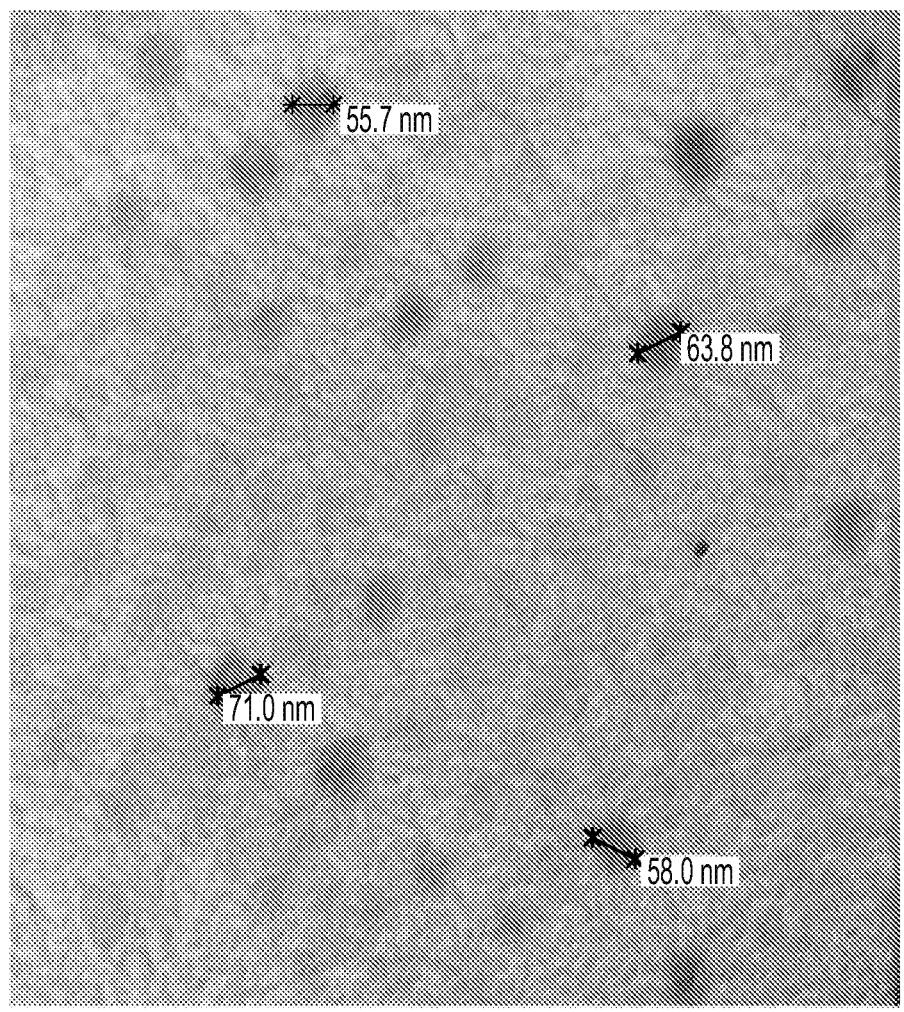
FIG. 10 Scanning microscopic image at 120000× mag demonstrating that adding equimolar amounts of cholesterol and homogenizing at 35,000 rpm for six minutes reduced the average size of the nanocarriers from about 150 nm to about 65 nm.

(e) UA-Nanocarrier Average Diameter is Reduced with Cholesterol and Homogenization A reduction in diameter was carried out by high pressure homogenization with cholesterol stabilization. Adding equimolar amounts of cholesterol and homogenizing at 35,000 rpm for six minutes reduced the average size of the nanocarriers from about 150 nm to about 65 nm, as shown in FIG. 10.

(f) mPEG-UA Nanocarriers for Photodynamic and Sonodynamic Generation of Reactive Oxygen Species (ROS) when Combined with Chemical Photo- or Sono-Sensitizers.

Figure 11:
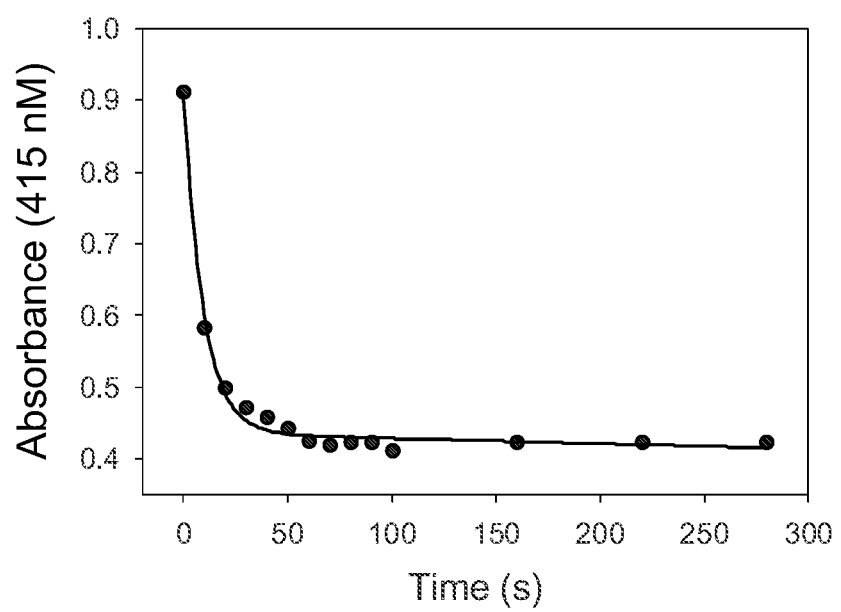
FIG. 11 Photodynamic ROS generated by irradiation of RGB LED's are detected by the DPBF assay. mPEG-UA nanocarriers are complexed with a photoreactive iron complex as a photosensitizer; graph shows decrease in ROS.
Figure 12:
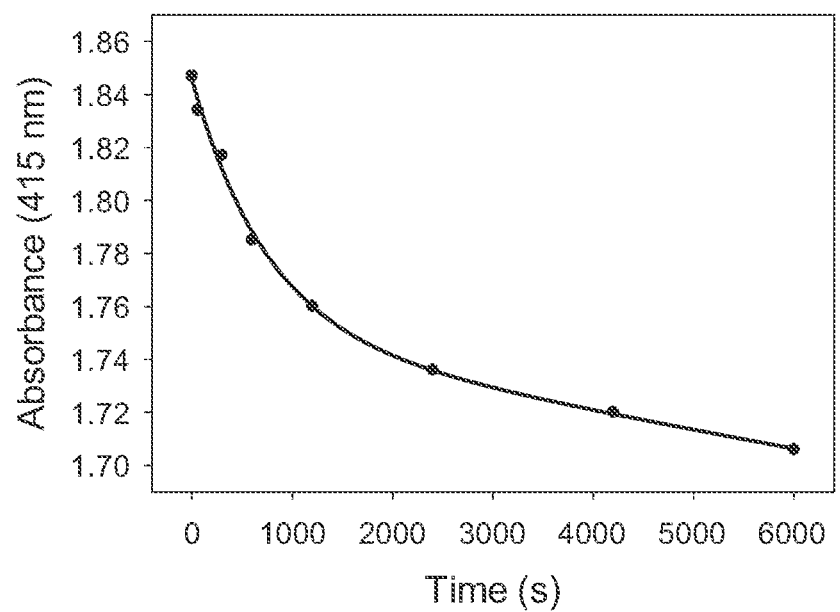
FIG. 12 Sonodynamic ROS generated by sonication at 1.0 MHz, 3 W/cm$^2$ of sodium copper chlorophyllin and detected by the DPBF assay. mPeg-UA nanocarriers are complexed with a sonoreactive copper complex as a sonosensitizer.
Figure 13:
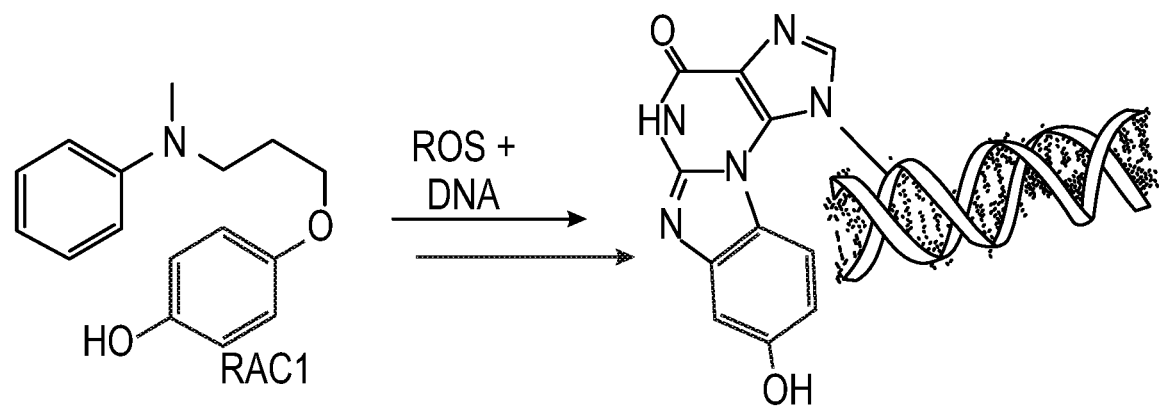
FIG. 13 Schematic showing ROS-activation of RAC1.
Figure 15A:
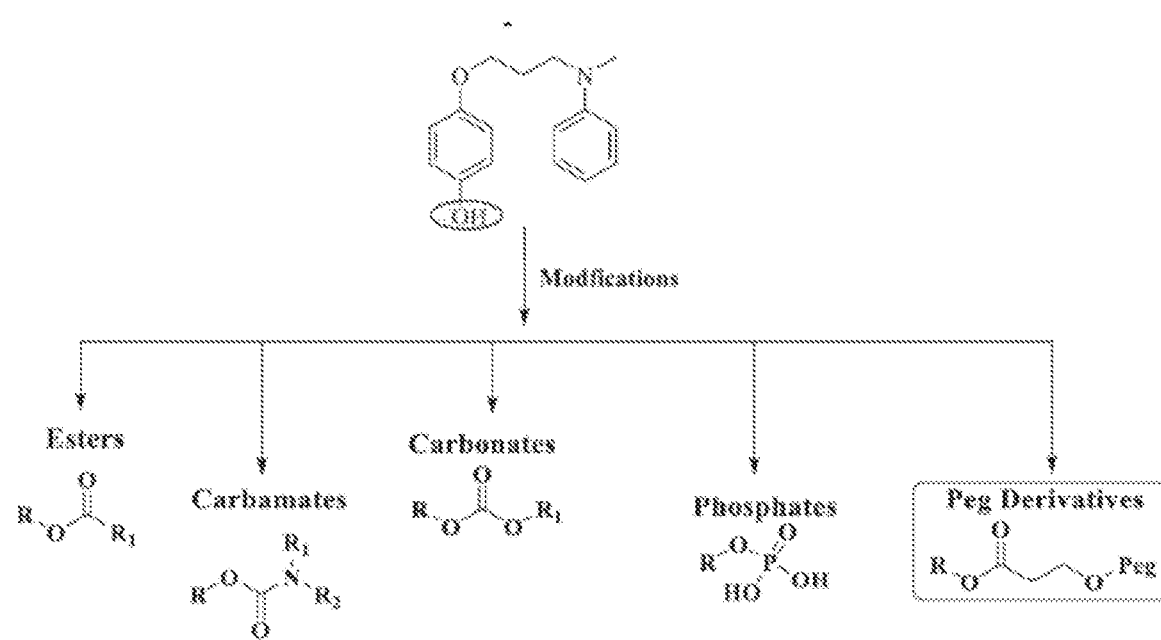
FIG. 15A Chart of chemical derivatization undertaken on the hydroxyl of Compound 8=RAC1

Photodynamic Reactive Oxygen Species (ROS) were generated by irradiation of red/green/blue (RGB) LEDs at 8 mW/cm$^2$ and detected by the 1,3-diphenylisobenzofuran (DPBF) assay. A photoreactive iron complex (Fe$_3$[diCl-Sal-AHA]$_3$OCH$_3$ Na) from the Baldwin Lab (UC Chemistry) was employed as the photosensitizer and complexed with the mPEG-UA nanocarrier vesicles. Results are set forth in FIG. 11 showing that photodynamic ROS are generated by irradiation of RGB LED's confirmed by detection using the DPBF assay. Sonodynamic ROS were generated by sonication at 1.0 MHz, 3 W/cm$^2$ of sodium copper chlorophyllin. mPeg-UA nanocarrier vesicles were complexed with the sonoreactive copper complex as a sonosensitizer and ROS were detected by the 1,3-diphenylisobenzofuran (DPBF) assay, as shown in FIG. 12.

Those skilled in the art will recognize, or be able to ascertain using no more than routine experimentation, many equivalents to the specific embodiments of the invention described herein. The scope of the present invention is not intended to be limited to the above Description and Examples, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given composition or method. The invention also includes embodiments in which more than one, or all group members are present in, employed in, or otherwise relevant to a given composition or method. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. It should also be understood that, in general, where the invention, or embodiments and aspects of the invention, is/are referred to as comprising particular elements, features, etc., certain embodiments of the invention or aspects of the invention consist, or consist essentially of, such elements, features, etc. "Consist essentially" in accordance with the disclosure means that in addition to the recited element(s), non-essential elements may or may not be present.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein.

What is claimed:

1. A targeted drug delivery system comprising a chemotherapeutic agent solubilized with undecylenic acid (UA)-based nanocarrier vesicles selected from polymeric UA-based nanocarrier vesicles, monomeric UA-based nanocarrier vesicles bonded to methoxy polyethylene glycol (mPEG), and polymeric UA-based nanocarrier vesicles bonded to mPEG, wherein the chemotherapeutic agent comprises at least one reactive oxygen species (ROS)-activated cytotoxic agent (RAC) and wherein the drug delivery system is formulated for intravenous injection or infusion.

2. The targeted drug delivery system according to claim 1, wherein an average hydrodynamic diameter of the nanocarrier vesicles is between about 5 nm and about 200 nm.

3. The targeted drug delivery system according to claim 1 comprising PEGylated UA-based nanocarrier vesicles having an average hydrodynamic diameter of about 65 nm.

4. The targeted drug delivery system according to 1, wherein the at least one RAC comprises a molecule selected from the group consisting of:

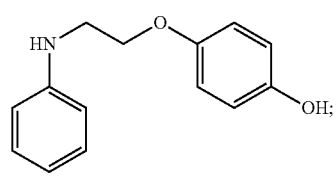

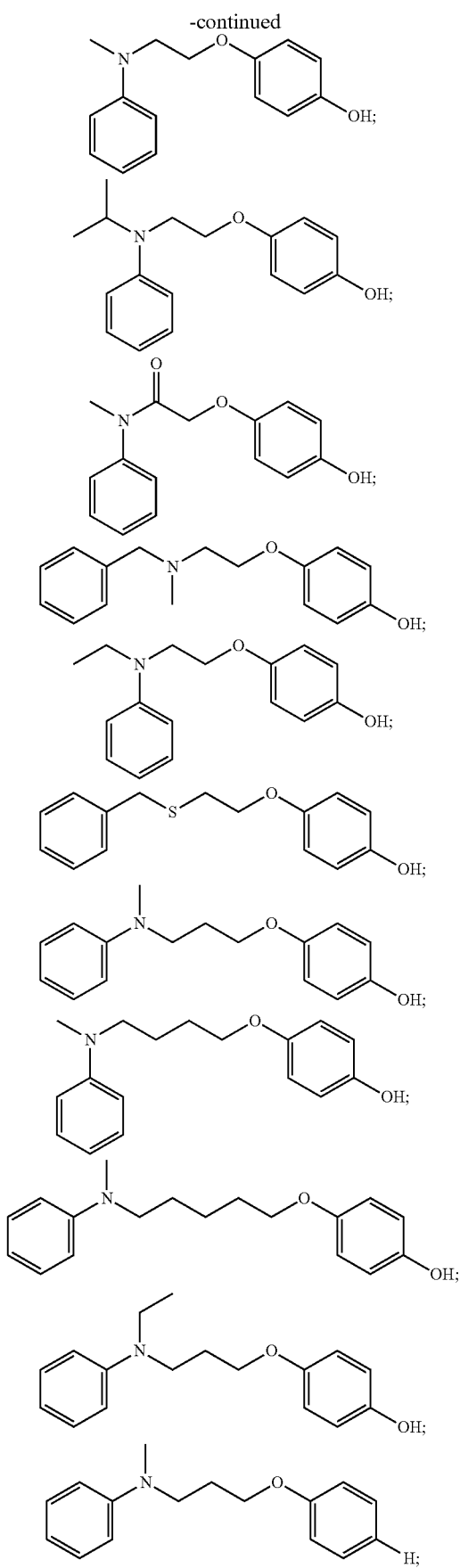
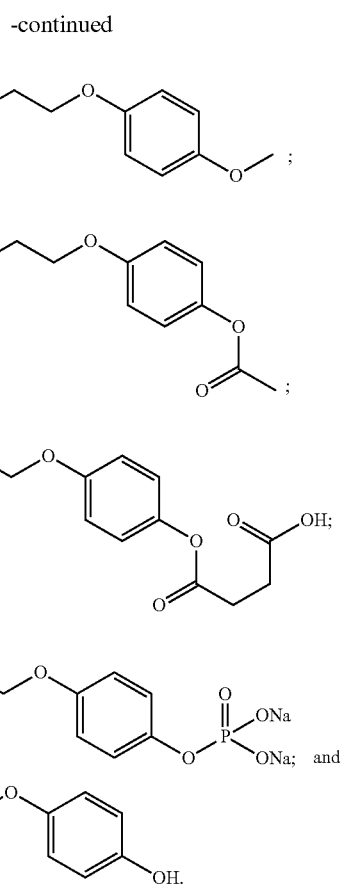
5. The targeted drug delivery system according to claim 4, wherein the at least one RAC comprises RAC1 and/or a derivative of RAC1.
6. The targeted drug delivery system according to claim 4, comprising at least one agent selected from the group consisting of:
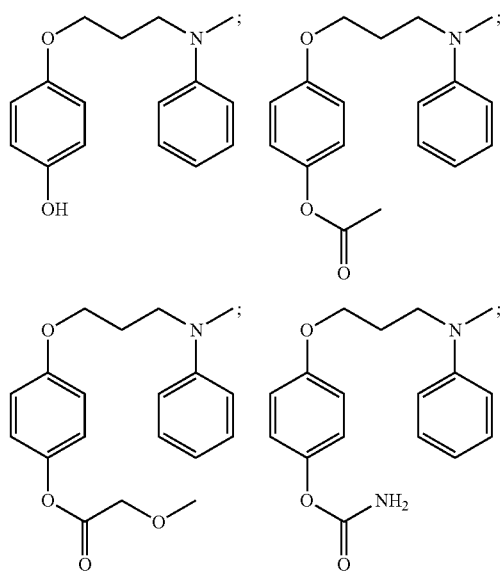

-continued

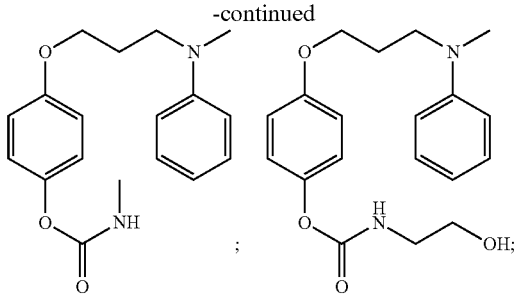

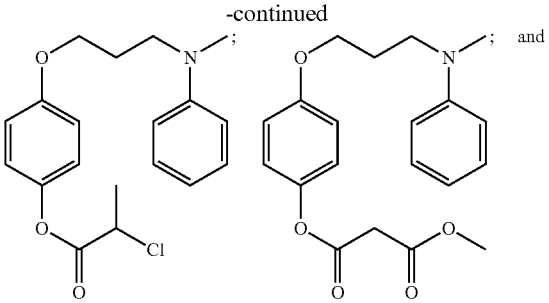

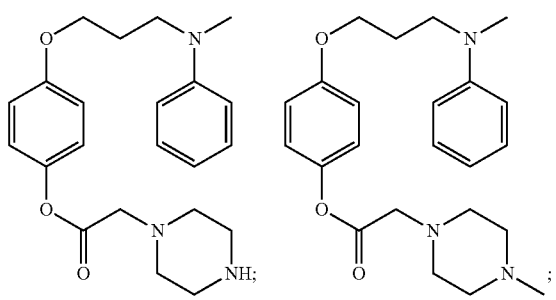

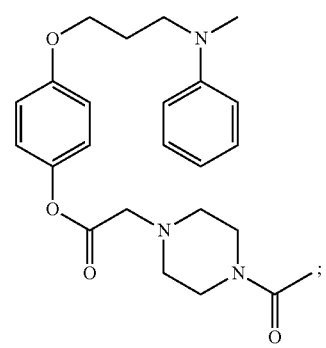

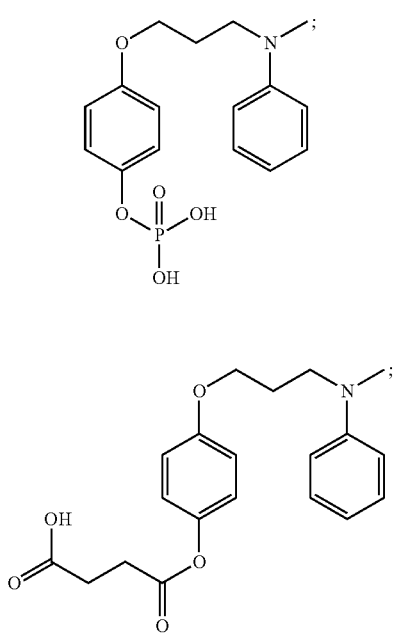

7. A pharmaceutical composition comprising a drug delivery system according to claim 1.

8. A method of treating a proliferative disorder associated with an increased presence of reactive oxygen species (ROS) in a subject in need thereof, the method comprising administering to the subject via intravenous injection or infusion a pharmaceutical composition comprising a targeted drug delivery system comprising a chemotherapeutic agent solubilized with undecylenic acid (UA)-based nanocarrier vesicles selected from polymeric UA-based nanocarrier vesicles, monomeric UA-based nanocarrier vesicles bonded to methoxy polyethylene glycol (mPEG), and polymeric UA-based nanocarrier vesicles bonded to mPEG, said vesicles having an average hydrodynamic diameter of between about 5 and 200 nm, wherein the chemotherapeutic agent comprises at least one ROS-activated cytotoxic agent (RAC).

9. The method according to claim 8, wherein the UA-based nanocarrier vesicle comprises PEGylated UA-based nanocarrier.

10. The method according to claim 8, wherein the proliferative disorder is selected from melanoma, prostate cancer, acute myeloid leukemia (AML), breast cancer, colon cancer, and ovarian cancer.

11. The method according to claim 10, wherein the proliferative disorder comprises AML.

12. The method according to claim 8, wherein at least one RAC comprises a molecule selected from the group consisting of:

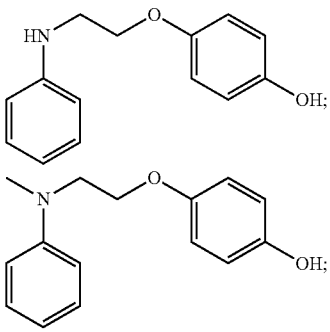

-continued
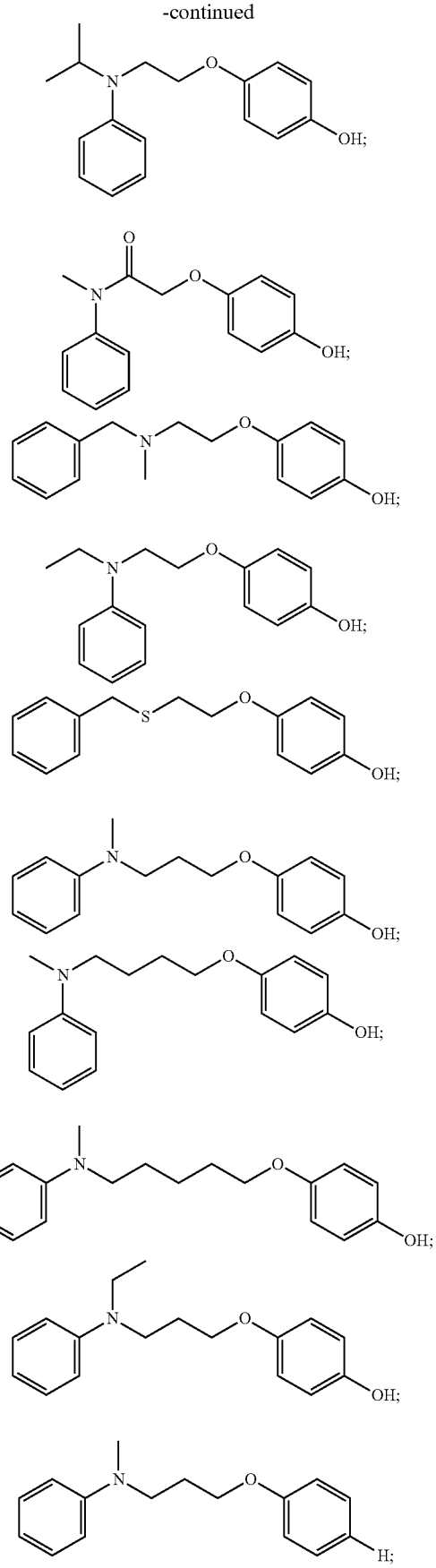
-continued
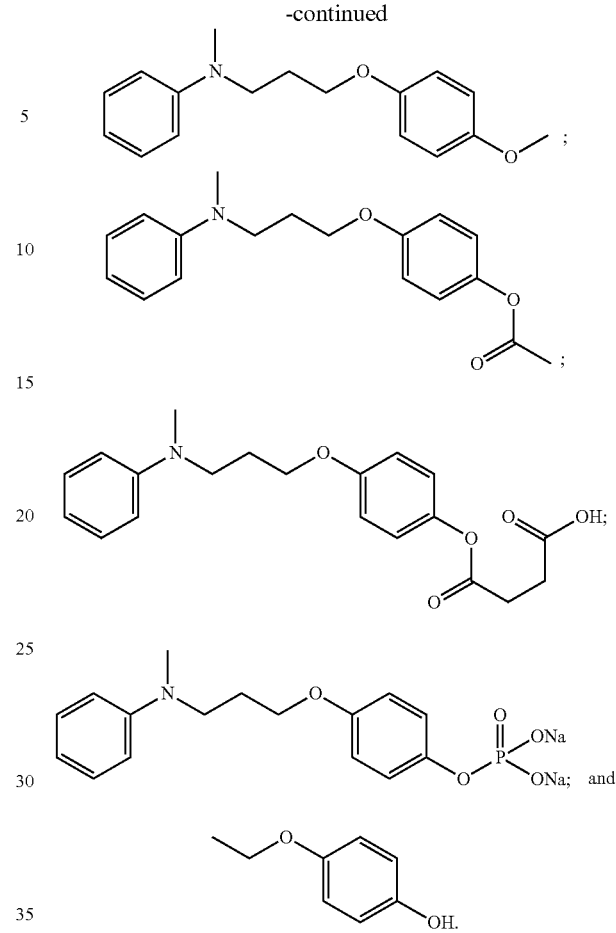
13. The method according to claim 12, wherein the RAC comprises RAC1 and/or a derivative of RAC1.
14. The method according to claim 13 comprising at least one agent selected from the group consisting of:
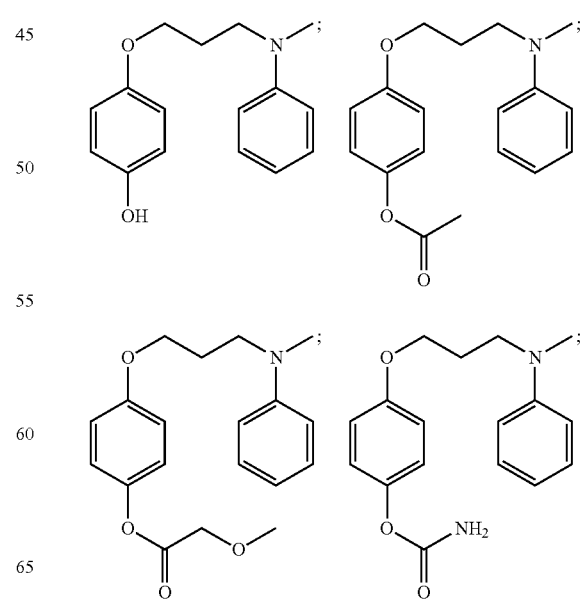

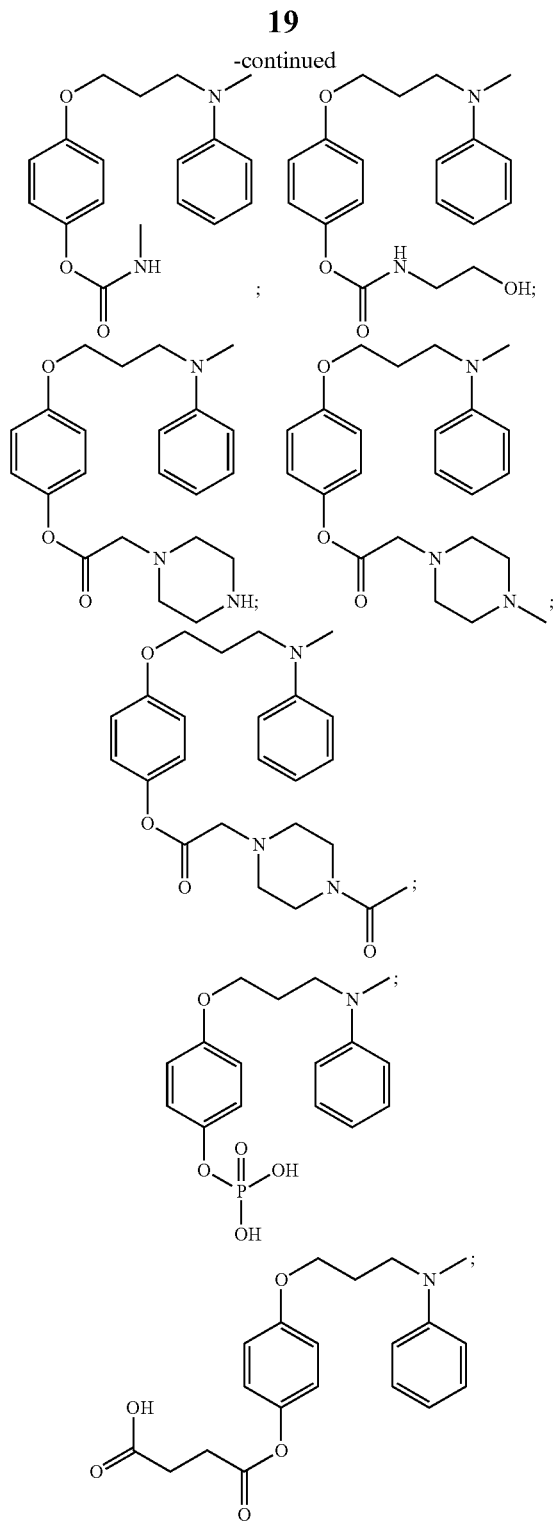

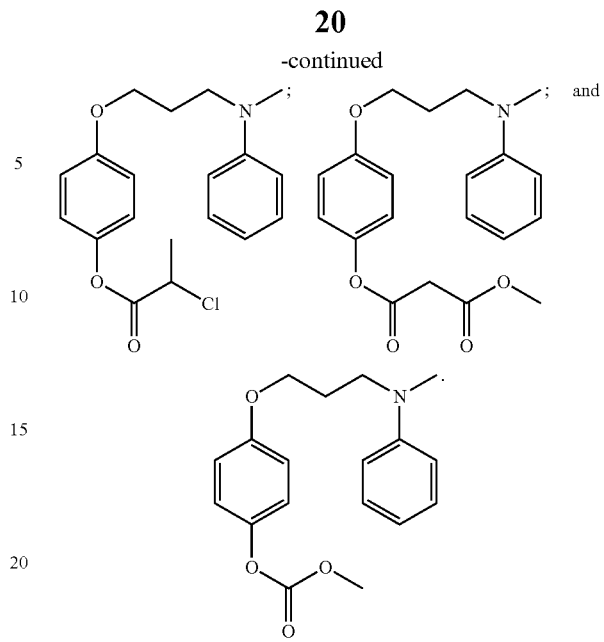

15. The method according to claim 8, further comprising administering at least one DNA-altering agent in conjunction with the pharmaceutical composition, wherein in conjunction with means as a part of a therapeutic regimen.

16. The method according to claim 15, wherein the at least one other DNA-altering agent comprises a DNA intercalator, a DNA metabolism inhibitor, and combinations thereof.

17. The method according to claim 16, wherein the DNA intercalator comprises one or more of daunorubicin and doxorubicin, and the DNA metabolism inhibitor comprises cytosine arabinoside.

18. A targeted drug delivery system comprising:
   a chemotherapeutic agent comprising at least one reactive oxygen species (ROS)-activated cytotoxic (RAC) agent, wherein the RAC agent is RAC1 or a derivative thereof; and
   a nanocarrier vesicle, wherein the nanocarrier vesicle comprises polymerized undecylenic acid, polymerized undecenoate, or methoxy polyethylene glycol (mPEG) esters of undecylenic acid,
wherein:
   the chemotherapeutic agent is solubilized in the nanocarrier vesicles;
   the nanocarrier vesicle protects the RAC agent from enzymatic degradation in the bloodstream; and
   the drug delivery system is formulated for intravenous injection or infusion.

\* \* \* \* \*